United States Patent [19]

Clark

[11] Patent Number: 5,643,273
[45] Date of Patent: Jul. 1, 1997

[54] ACL BONE TUNNEL PROJECTION DRILL GUIDE AND METHOD FOR ITS USE

[76] Inventor: Ron Clark, 1184 E. 80 North, American Fork, Utah 84003-2968

[21] Appl. No.: 390,872

[22] Filed: Feb. 17, 1995

[51] Int. Cl.⁶ .................................................. A61B 17/56
[52] U.S. Cl. ............................................. 606/96; 606/102
[58] Field of Search ................................. 606/96, 97, 98, 606/86, 80, 102, 103, 74, 53

[56] References Cited

U.S. PATENT DOCUMENTS

| | | |
|---|---|---|
| 2,131,321 | 9/1938 | Hart . |
| 2,595,086 | 4/1952 | Larazelere . |
| 3,665,926 | 5/1972 | Flores . |
| 3,727,611 | 4/1973 | Schultz . |
| 4,257,411 | 3/1981 | Cho . |
| 4,509,516 | 4/1985 | Richmond . |
| 4,535,768 | 8/1985 | Hourahane et al. . |
| 4,597,390 | 7/1986 | Mulhollan et al. . |
| 4,672,957 | 6/1987 | Hourahane . |
| 4,708,139 | 11/1987 | Dunbar, IV . |
| 4,739,751 | 4/1988 | Sapega et al. . |
| 4,772,286 | 9/1988 | Goble et al. . |
| 4,781,182 | 11/1988 | Purnell et al. . |
| 4,787,377 | 11/1988 | Laboureau . |
| 4,823,780 | 4/1989 | Odensten et al. . |
| 4,901,711 | 2/1990 | Goble et al. . |
| 4,920,958 | 5/1990 | Walt et al. . |
| 4,923,461 | 5/1990 | Caspari et al. . |
| 4,985,032 | 1/1991 | Goble et al. . |
| 5,034,012 | 7/1991 | Frigg . |
| 5,129,902 | 7/1992 | Goble et al. . |
| 5,139,520 | 8/1992 | Rosenberg . |
| 5,144,961 | 9/1992 | Chen et al. . |
| 5,147,362 | 9/1992 | Goble et al. . |
| 5,152,764 | 10/1992 | Goble et al. . |
| 5,234,434 | 8/1993 | Goble et al. . |
| 5,266,075 | 11/1993 | Clark et al. . |
| 5,314,429 | 5/1994 | Goble . |
| 5,485,602 | 1/1996 | Goble et al. ........................ 606/96 |
| 5,562,664 | 10/1996 | Durlacher et al. ................. 606/96 |
| 5,562,675 | 10/1996 | McNulty et al. .................... 606/96 |

FOREIGN PATENT DOCUMENTS 552077  7/1975  Russian Federation .

OTHER PUBLICATIONS

Shaffer et al. "Graft-Tunnel . . . Harvesting" Arthroscopy, 9(6):633–646 Dec. 1993.
The Arthrex Transtibial System Brochure, 1992, Author Unknown, 2 pages.
Protrac / Acufex Microsurgical, Inc. Brochure, Author and Date Unknown, 1 page.

Primary Examiner—Guy V. Tucker
Attorney, Agent, or Firm—M. Reid Russell

[57] ABSTRACT

An ACL bone tunnel projection drill guide and method for its use that includes a body configured to by held by a surgeon that includes a straight wire guide tube secured to extend, at approximately a right angle outwardly, from a lower end thereof and contains an arcuate slot formed therein to receive a radial arm fitted to slide in and out therefrom. A drill tube mount is secured across an end of the radial arm that includes a longitudinal passage wherethrough a barrel is fitted to be installed into a tibial tunnel section formed in a patient's proximal tibial in an anterior cruciate ligament replacement procedure. The wire guide tube contains a connecting wire that connects, on a distal end to a straight articulating tip pivotally connected to the wire guide tube distal end, and is fitted over at least one roller to extend to pivot the articulating tip when the radial arm travels out of the body arcuate slot. Which wire guide tube also includes a projecting wire fitted into the articulating tip to extend therefrom when an actuator slide fitted in a slot in the body, whereto the projecting wire proximal end is attached, is moved. The length of projecting wire extension is determined by a comparison of an indicator on the actuator slide with marking on a scale scribe alongside of the slot. With the articulating tip proximal end maintained at the tibial tunnel section end, the determination of the length of projecting wire extension along with the length of that articulating tip determines the distance between the tibial tunnel section end and a point along the femur intercondylar notch contacted by the projecting wire end, which distance is used by a surgeon to select and appropriate length of a replacement ligament graft.

12 Claims, 4 Drawing Sheets

ACL BONE TUNNEL PROJECTION DRILL GUIDE AND METHOD FOR ITS USE

BACKGROUND OF THE INVENTION

1. Field of the Invention

This invention relates to devices and procedures for their use in an arthroscopic surgical procedure involving forming a straight ligament tunnel in a procedure for replacing a knee anterior cruciate ligament determining tunnel lengths and distance across the knee intra articular joint for selecting an appropriate length of a replacement ligament.

2. Prior Art

The present invention is in a device and its use with a surgical procedure involving formation of a straight tunnel in the distal femur and proximal tibia for replacing a patient's anterior cruciate ligament. The invention for use for conveniently locating a point on the surface of a patent's distal femur in their intercondylar notch that is to be a femoral tunnel end for measuring the distance between the points of origin of the anterior cruciate ligament, and the lengths of the femoral and tibial tunnel sections of the straight for selecting of a proper length of a replacement ligament. The located point to receive a straight pin turned therein to serve as a guide to receive one or more cannulated drills turned thereover to form a straight femoral tunnel section that is an extension of a tibial tunnel formed from the through proximal tibial, exiting within the knee intra articular joint. In which tunnel formation, the drilled hole or tunnel will pass through femur and tibia points of ligament origin. The prepared straight hole or tunnel is then for receiving the selected natural or prosthetic ligament fitted and secured therein in a surgical procedure for replacing a knee anterior cruciate ligament.

In the field of arthroscopic surgery, a procedure has recently been developed where, with a patient's knee bent at appropriately ninety degrees (90°), a straight tunnel is formed through the tibial tuberosity, extending across the anterior cruciate points of origin in the intra articular joint on the proximal tibia and distal femur surfaces, and into the femur endosteum. Thereafter, an end of a replacement ligament, that is either a natural or prosthetic ligament, is fitted through the tibial opening to travel along the tunnel for mounting in the femur endosteum. One such use of a straight tunnel and mounting for an anterior cruciate ligament in the femur endosteum end thereof is shown in an earlier patent of the present inventor and others, Clark, et al, U.S. Pat. No. 5,266,075. Also, other examples of such straight tunnel formation procedures and a use of connectors for endosteally mounting a ligament end in a femoral tunnel section are shown in patents to Goble, et al, U.S. Pat. Nos. 4,772,286; 5,129,902 and 5,147,362. Further, a number of drill guides for forming such straight tibial and femoral tunnel sections in an arthroscopic surgical procedure are shown in patents to Goble, et al, U.S. Pat. Nos. 4,985,032; 4,901,711; 5,152,764; and 5,234,434. Also, another Goble U.S. Pat. No. 5,314,429, shows a guide for guiding drilling to a location along such straight ligament tunnel. None of which connectors and drill guide arrangements, however, show an arrangement for measuring the distance from the ligament points of origin and tunnel section lengths from the proximal tibia to a location in the distal femur for selecting an appropriate length of replacement ligament.

Additional to the Goble, et al drill guides, as set out above, there are a number of instruments for use in arthroscopic surgical procedures for guiding drilling to a location in a patient's knee. For example, U.S. Pat. Nos. 4,535,768; 4,672,957; 4,708,139; 4,739,751; 4,781,182; 4,787,377; 4,823,780; and 4,920,958, show examples of drill guides for forming a hole into a knee to a location therein that a pointer end of an arm of the drill guide is located. None, however, provide an arrangement, as does the present invention, for both locating a point on a distal femur surface as a ligament point of origin that aligns with a drill tube of the invention that has been fitted into a tibial tunnel, and for measuring the distance between the tibial tunnel end in the intra articular joint and that located point for selecting an appropriate length of replacement ligament. Further, which projecting wire end can be used to mark the location on the femur that then receives a k-wire that is turned into the distal femur to receive one or more cannulated drills turned therealong. The cannulated drills form a straight hole into the distal femur to receive a replacement anterior cruciate ligament, that is either natural or prosthetic, fitted therein. The length of which femoral tunnel section is itself easily determined by a subtraction of the length of the tibial tunnel section determined off from a scale marked on a drill guide and the distance across the intra articular joint between the ligament points of origin from the length of the drill turned into the distal femur the forms the femoral tunnel section.

SUMMARY OF THE INVENTION

It is a principal object of the present invention in a tunnel projection drill guide to provide a device for use in an knee arthroscopic surgical procedure for both locating a point on a distal femur surface that is opposite to the end of a proximal tibia tunnel as a femoral point of ligament origin, and determining the distance between which tibial tunnel end in the knee intra articular joint and the femoral point of ligament origin for selecting a proper length of ligament graft.

Another object of the present invention in a tunnel projection drill guide is to provide, for measuring the distance between the ligament points of origin, a capability for pivoting an articulating tip end of a wire guide tube of the drilling guide when it is within the knee to an angle that aligns with the longitudinal axis of a drill guide barrel inserted into the knee joint.

Another object of the present invention in a tunnel projection drill guide is to provide, a pivoting fin maintained to which articulating tip to extend rearwardly therefrom when the articulating tip is pivoted within knee, function as a stylus to engage the tibial tunnel end.

Another object of the present invention in a tunnel projection drill guide is to provide, for measuring the distance between the ligament points of origin, a scale scribed along an arcuate arm that has been fitted into to slide within a track formed in a body of the guide that mounts the drill guide barrel on one end, which arcuate arm connects to a proximal end of the wire whose distal end is connected to the articulating tip whereby travel of the arcuate arm to move the drill guide barrel away from the body moves the articulating tip such the drill guide barrel continually aligns with a cylinder of the articulating tip, the scale providing a visual representation of the angle the articulating arm is moved away from the wire guide tube.

Still another object of the present invention in a tunnel projection drill guide is to provide for linking the articulating tip of the wire guide tube through to the arcuate arm such that the arcuate arm travel from the body will pivot the articulating tip to the angle that the drill guide barrel is moved away from the body end.

Still another object of the present invention in a tunnel projection drill guide is to provide, for projection from the articulating tip of the wire guide tube, a projecting wire for extension out from the distal end of the wire guide tube articulating tip that will travel across the patient's knee intra articular joint and contact a point in the opposing femur intercondylar notch, for determining the distance between the femoral and tibial points of ligament origin.

Still another object of the present invention in a tunnel projection drill guide is to provide, utilizing the projecting wire end, for marking the point of contact within the intercondylar notch to receive a k-wire, or the like, later fitted through a drill guide arranged in the tibial tunnel and turned into the distal femur, the k-wire to guide turning of one or more cannulated drills therealong forming a straight femoral tunnel section that will exactly aligns with the tibial tunnel section, forming a straight ligament tunnel.

Still another object of the present invention in a tunnel projection drill guide is to provide a guide that includes a body that is arranged to be held by a surgeon performing an anterior cruciate ligament reconstructive procedure who, by moving a slide along a track formed in the body can extend the projecting wire out of the distal end of a wire guide tube articulating tip, the projecting wire to extend across the patient's between a straight tibial tunnel and a point along the femur intercondylar notch, the slide positioning along the track when compared with a scale marked along which track providing a measure of the distance between the tibial tunnel end within the intra articular joint and the selected point on the distal femur intercondylar notch for use in selecting a proper length of a replacement ligament, that located point to receive a guide wire turned into the distal femur that is to receive and guide one or more cannulated drills turned thereon to form the femoral tunnel section.

Still another object of the present invention in a tunnel projection drill guide is to provide a guide that is easy and convenient to use by a surgeon in the performance of an anterior cruciate ligament replacement procedure for determining a distance between the tibial tunnel end within the knee intra articular joint and a selected point along the distal femur intercondylar notch for selecting an appropriate length of replacement ligament, and for marking that located point along the distal femur to receive a k-wire, or the like, turned into the femur endosteum used for guiding one or more cannulated drills fitted thereover and turned into the distal femur, forming a straight femoral tunnel section that exactly aligns with a straight tibial tunnel section to receive a ligament graft fitted and secured therein.

The present invention is in a drill guide type device includes a body for gripping by a surgeon for use in an arthroscopic surgical procedure for replacing a patient's anterior cruciate ligament. The tunnel projection drill guide of the includes an articulating arm arranged to slide in and out of the body that mounts, on its distal end a drill tube mount that references a straight tunnel formed in the patient's proximal tibia. The tibial tunnel is drilled from the tibial tuberosity into the intra articular joint, the tunnel exit constituting a tibial ligament point of origin on the proximal tibia surface. The formed tibial tunnel receives a straight open tube of a drill tube mount fitted into the tibial tunnel after an articulating tip end of a straight wire guide tube that extends from the body is inserted through an arthroscopic portal formed into the patient's knee into the intra articular joint. The drill tube mount is arranged to slide within an arcuate chamber or slot formed in the guide body.

The guide body, additional to being formed to be comfortable gripping by the surgeon, contains the articulating arm arranged to be pulled in and out thereof that mounts the drill tube mount, provides an end surface for comparison with a scale marked along the articulating arm whereby the surgeon, aligning a scale marking with the end of the guide body, reads therefrom the arcuate angle of the open drill guide tube and the wire guide tube.

The wire guide tube extends, at approximately a right angle, from the guide body, is in the plane of the drill tube mount and includes, on a distal end thereof, a pivoting articulating tip. A pair of individual wires extend from the guide body and through the wire guide barrel. One of which wires is a connecting wire that connects at one end, to the articulating tip and is passed through a roller mechanism and connects to the radial arm, with the roller mechanism also maintained to the radial arm. Movement of which connecting wire is provided by moving the radial arm in and out of the body provides for pivoting the articulating tip. So arranged, the articulating tip is pivoted to an angle from the wire guide barrel longitudinal axis that is the same angle as the drill tube mount is positioned relative to the guide body end.

In operation, a barrel of the guide tube mount will, at all times during arcuate arm travel from and into the body, point at an open cylinder of the wire guide tube articulating tip. A second wire is a projecting wire that is arranged to extend from the body through the wire guide tube, and into the articulating tip, to project therefrom. A proximal end of the projecting wire is attached to a slide to be moved by a surgeon holding the body that travels along a track formed in a top side of the guide body. The distance the projecting wire extends from the articulating tip is used to calculate the length of a replacement ligament, and the projecting wire distal end may be sharp to mark a point along the distal femur intercondylar notch as a femoral point of ligament origin. A scale is scribed along a track edge alongside the slide that the surgeon compares the slide position with to determine the distance the projecting wire extended from the articulating tip to the intercondylar notch. Accordingly, a surgeon, using their thumb, moves the slide along the guide body track to extend the connected projecting wire end out of the articulating tip distal end. Taking into account the length of the articulating tip that is seated at the tibial tunnel end and the length of projecting wire extended from across tip the distance across the patient's knee intra articular joint between the ligament points of origin it determined. Which distance is determined by the surgeon, who compares the slide location along the track with a scale marking. With this distance and by a reading of a scale marked along a barrel of the drill tube mount and length of the femoral tunnel section, formed as set out below, a surgeon determines a correct length of a replacement ligament, that can be either a natural or prosthetic ligament, to span between femoral and tibial tunnel sections as a replacement for the patient's anterior cruciate ligament.

As set out above, the wire guide tube articulating tip pivots as the radial arm travels back and forth in the guide body cavity. A cylinder of the articulating tip provides a passage wherethrough the projecting wire extends. Which cylinder will be axially aligned with the drill tube mount barrel that is fitted within the tibial tunnel section. In operation, the lower or proximal end of which articulating tip is maintained at the tibial tunnel end. To so provide, the articulating tip proximal end includes a fin secured to the undersurface thereof whose end will serve as a stylus extending oppositely to the articulating tip to engage the tibial tunnel end for holding the articulating tip thereat while the projecting wire is extended out from the articulating tip end, as describe above.

The projecting wire end contacts with a point in the intercondylar notch, establishes the distance the projecting wire has extended, and that wire end contact can provide for marking the distal femur point of ligament origin to receive an end of a k-wire, or the like, for turning therein that is to serve as a guide for turning one or more cannulated drills thereover into the distal femur endosteum forming the femoral tunnel section.

The present invention provides a device and method for conveniently determining the distance between the femoral and tibial tunnel ends, that are the ligament points of origin for use in determining a proper length of a replacement ligament graft for use in the surgical procedure to replace the patient's anterior cruciate ligament.

DESCRIPTION OF THE DRAWINGS

In the drawings that illustrate that which is presently regarded as the best mode for carrying out the invention.

DETAILED DESCRIPTION

Figure 1:
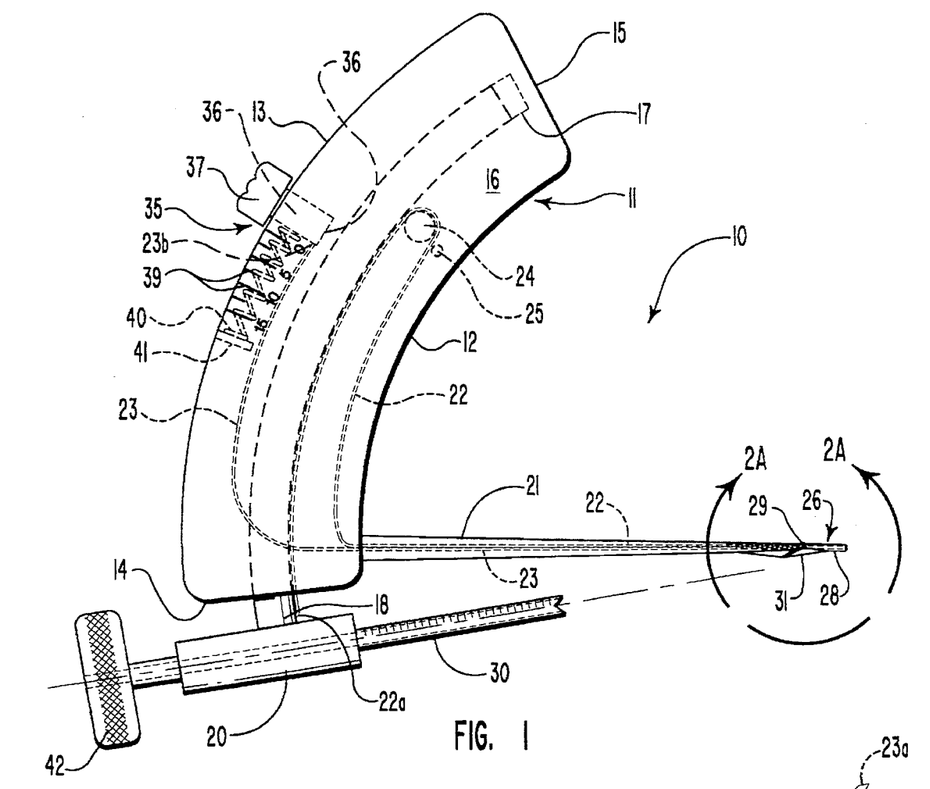
FIG. 1 is a top plan view a tunnel projection drill guide of the invention that includes a body wherein a sliding radial arm is fitted that incorporates a drill tube mount, with a wire guide tube shown extending from the body end that contains movable connecting and projecting wires, shown in broken lines.
Figure 2A:
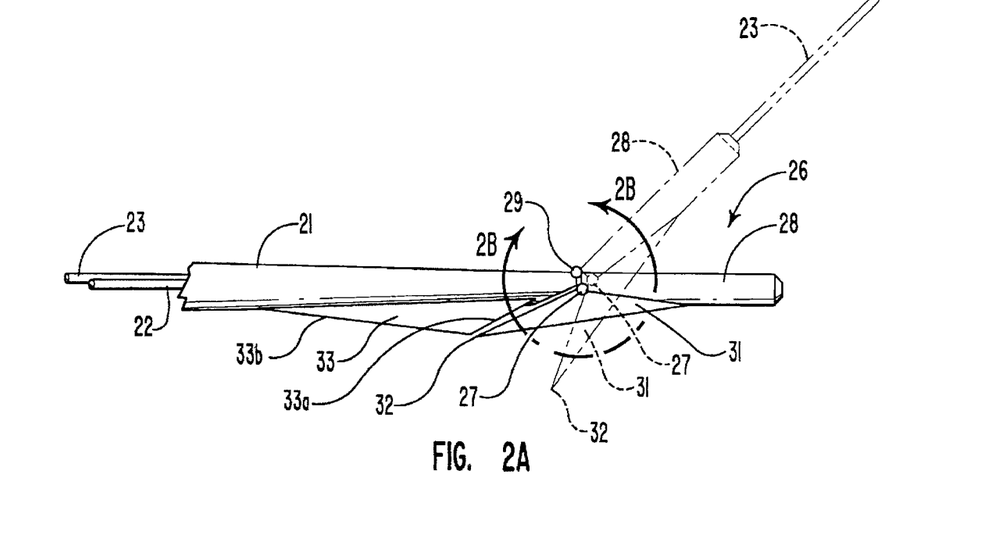
FIG. 2A is a view of a wire guide tube removed from the projector tunnel drilling guide body of FIG. 1, showing, in broken lines, an articulating tip that is pivotally connected to the wire guide tube distal end and has been rotated approximately forty five degrees (45°) from the wire guide tube longitudinal axis, showing a fin section thereof projecting downwardly, and a distal end of the projecting wire extending therefrom.
Figure 2B:
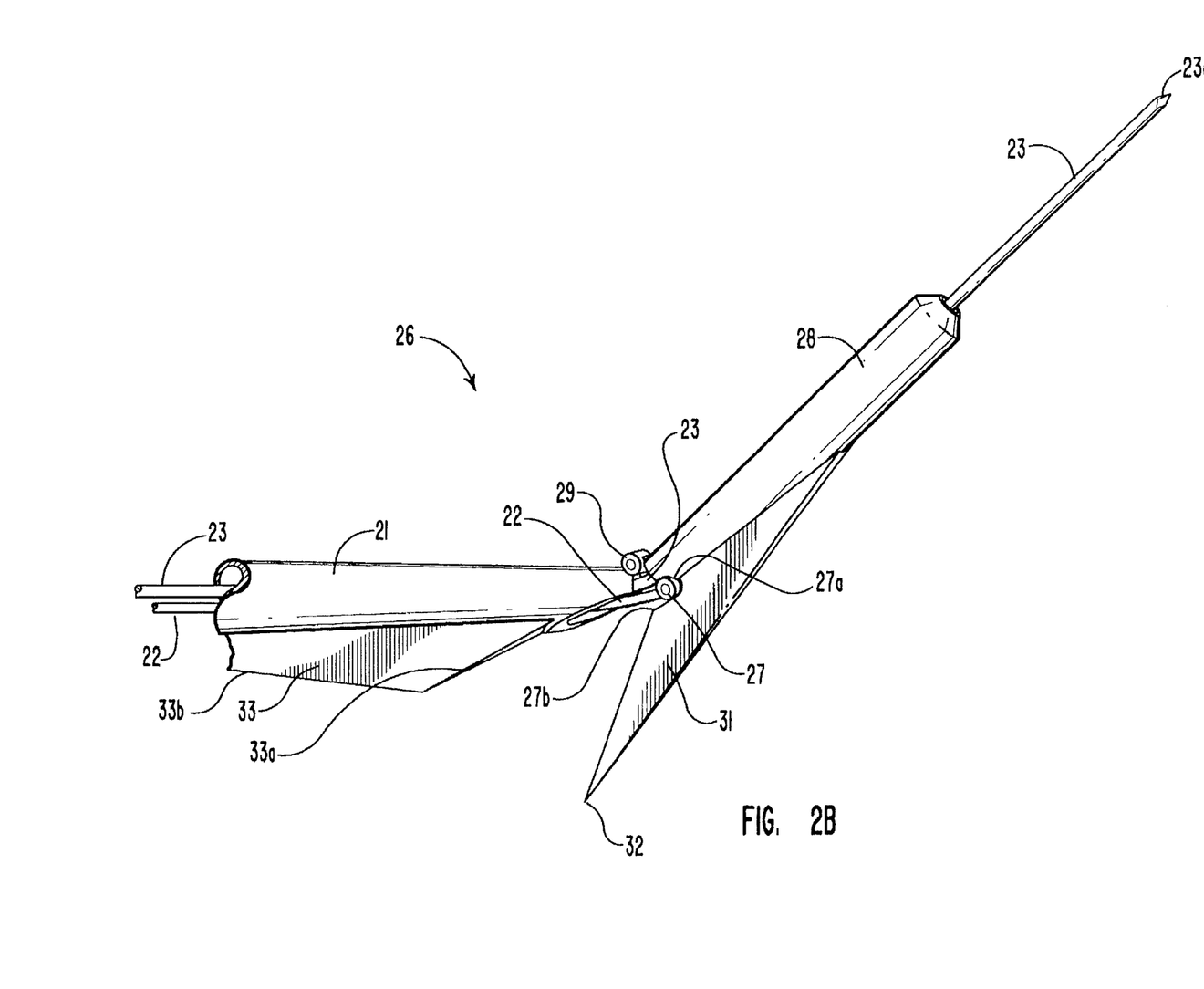
FIG. 2B is an enlarged sectional view taken within the line 2B—2B of FIG. 2, showing a bead end of the connecting wire fitted into a cup maintained in the proximal end of the articulating tip.
Figure 3:
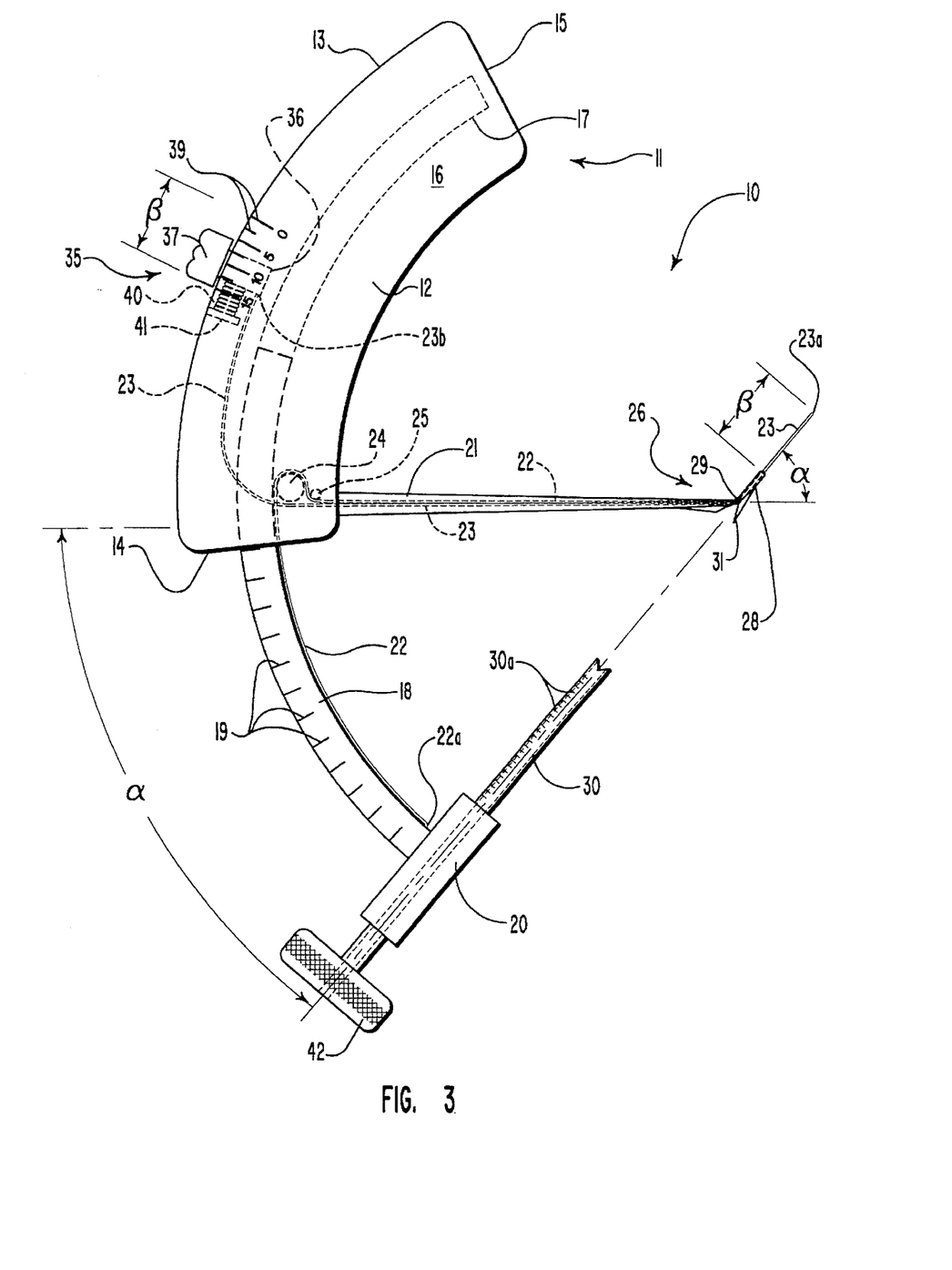
FIG. 3 is an enlarged view of the projector tunnel drill guide of FIG. 1 showing the sliding radial arm pulled outwardly from the end of a guide body, with the wire guide tube articulating tip shown pivoted from the wire guide tube longitudinal axis, and showing the projecting wire extending outwardly from the articulating tip distal end.
Figure 4:
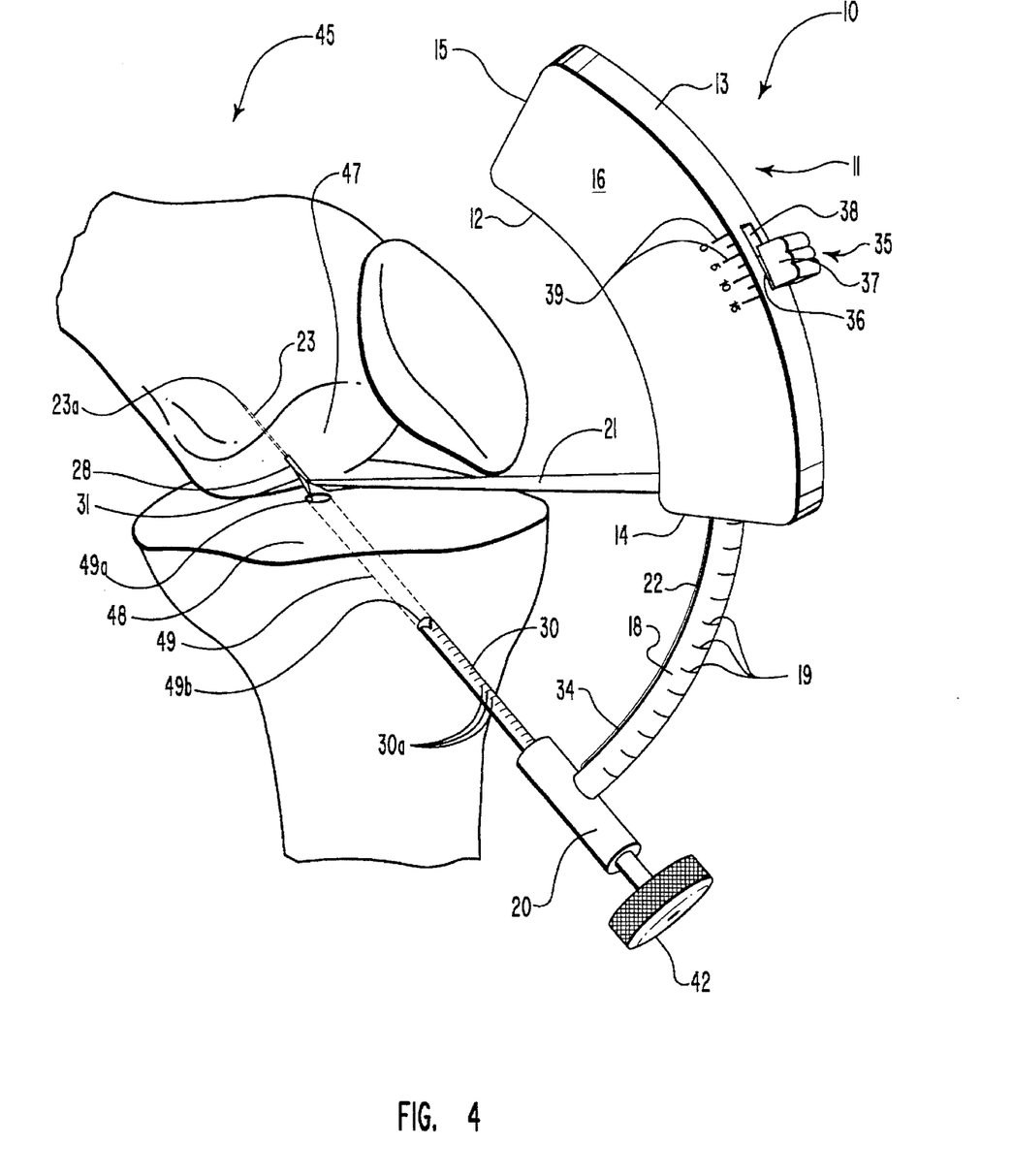
FIG. 4 shows the projector tunnel drill guide of FIGS. 1 and 3 being used in a medical procedure for determining a distance across a patient's knee between ligament points of origin to select a proper length of a ligament graft for use in a surgical procedure to replace the anterior cruciate ligament.

A projector tunnel drill guide 10 of the invention is shown in FIGS. 1 through 3 and its use is illustrated in FIG. 4, and is hereinafter referred to as guide 10. Guide 10, shown best in FIGS. 1 and 3 includes a body 11 that has forward and rear flat narrow arcuate shaped sides 12 and 13, respectively, that are each formed to have essentially the same arc. Straight equal length bottom and top ends 14 and 15 extend between the ends of sides 12 and 13 and the body 11 has flat opposing top and bottom faces 16. As shown, the body 11 preferably has essentially a rectangular cross section, and is of thickness and width to conveniently fit into in the palm of a surgeon/operator's hand.

Shown in broken lines in FIGS. 1 and 3, an arcuate slot 17, having a rectangular cross section, is formed in the body 11, extending nearly the length thereof and has essentially the same arc as the sides 12 and 13. The arcuate slot 17 is to receive a radial arm 18 to slide therein. The radial arm has essentially the same arc as does the arcuate slot 17 and sides 12 and 13, and is shaped to have a uniform rectangular cross section to slide along the arcuate slot 17. Equal spaced lateral scale markings 19, that represent increasing degrees or arc are scribed along the radial arm 18. In the operation of the guide 10, as set out hereinbelow, which scale allows the surgeon to read off therefrom an arc of up to seventy-five degrees (75°), shown as angle alpha ($\alpha$) in FIG. 3, that is the angle between a drill tube mount 20 and a straight wire guide tube 21. Which drill tube mount 20, that is a cylindrical sleeve, is secured across a distal end of the radial arm, at a right angle thereto, and the straight wire guide tube 21 extends, at approximately a right angle, from the forward side 12 of body 11, proximate to the body bottom end 13. The wire guide tube 21, as shown, houses and provides an internal passage or track wherein a connecting wire 22 and a projecting wire 23 are both fitted to slide. The connecting wire 22, as shown is secured at a proximal end 22a to the articulating arm, proximate to the coupling with the drill tube mount, and therefrom extends along the radial arm inner surface 18a to pass over a first guide roller 24 and under a second positioning roller 25, as shown in broken lines. As shown in a comparison of FIGS. 1 and 3, the guide and positioning rollers 24 and 25 are mounted in the body 11 such that, with the radial arm 18 pulled fully out of the body 11, the connecting wire 22, operating through the wire guide tube 21 proximal end, will have pulled on to pivot the articulating tip 26 to the attitude shown in FIG. 3. In which attitude, a greatest angle alpha ($\alpha$) is formed between the drill tube mount 20 and wire guide tube 21, and an articulating tip 26, that is pivotally connected to the distal end of the wire guide tube 21, is pivoted to a like angle alpha ($\alpha$), as discussed below. Whereas, with the articulating arm 18 retracted into the body 11, the connecting wire 22 is also retracted so as to pivot the articulating tip 26 to where a cylinder 28 thereof will essentially align with the wire guide tube 21.

The coupling wire 22 extends through the wire guide tube 21 and, for coupling to the articulating tip 26, shown in broken lines in FIG. 2, includes a bead 27 secured to the distal end thereof. A pivot 29 is arranged between butting top edges of the wire guide tube distal end and the proximal end of the articulating tip 26. To provide for connecting the connecting wire 23 at bead 27, opposing spaced walls 27a are provided, as shown in FIG. 2A, that include opposing concave surfaces that function as a cup, and are located at the articulating tip proximal end, below the pivot 29. A rear of which pair of walls 27a is slotted to receive the connecting wire passed therealong, positioning the bead 27 between which walls, in their opposing concave walls that function as a cup, maintaining the bead therein. So arranged, pushing or pulling of the bead 27 by travel of the connecting wire causes the bead to push against the forward wall 27a pivoting the articulating tip to an angle from the longitudinal axis of the wire guide tube 21. With, when the bead is pulled against the rear wall 27a, the articulating tip 26 is returned to the attitude shown in FIG. 1. Thereby, pushing or pulling the connecting wire 22 through the wire guide tube 21 pivots the articulating tip 26 between the attitudes shown in FIGS. 1 through 4. The mounting of the connecting wire 22 to the radial arm 18 and the mounting of and the distance over the first roller 24 and under the second roller 25 to provide an extension of the connecting wire when the articulating arm is pulled out of the body 11, as shown best in FIG. 3.

Movement of the radial arm 18 out of the body 11, as shown in FIG. 3, thereby pivots the articulating arm 26 around pivot 29, as shown in FIG. 2, to an angle from the wire guide tube 21 longitudinal axis that is the arcuate angle alpha ($\alpha$) that the drill tube mount 20 makes to the wire guide tube 21. Accordingly, a straight wire passed through a drill tube mount barrel 30, as shown in FIG. 3, will exactly align with the projecting wire 23 that extends axially from the distal end of the articulating tip cylinder 28, as set out below.

Additional to pivot 29, and along the opposite edge thereto, the articulating tip cylinder 28 includes a fin 31, shown as a regular triangle, having two oppositely sloping sides that meet in an apex, one or a first of which sides thereof is secured to the surface of the articulating tip cylinder, to be parallel to the cylinder longitudinal axis. So arranged, the other or second of the two triangle sloping sides extends away from the articulating tip cylinder 28 proximal end, and the junction of the regular triangle base and that other or second opposite side forms a spike or stylus end 32. Which spike or stylus end 32 will enter a tibial tunnel distal end 49b, as shown in FIG. 4, during a surgical procedure utilizing guide 10, as set out hereinbelow. When, however, the fin is retracted to the attitude shown in FIGS. 1 and 2, the regular triangle other or second sloping side and spike end 32 will be retracted against a sloping side 33a of a triangular shaped outwardly projecting fence 33. With the other triangle fence side 33b connecting into the side of an inwardly sloping distal end section of the wire guide tube 21. So arranged, with the fin 31 retracted, as shown in FIG. 1, a smooth transition is provided between the aligned fin 31 and fence 33, allowing the wire guide tube 21 to be easily inserted into and pulled out from between the patient's knee intra articular joint during a surgical procedure utilizing the guide 10 of the invention.

As set out above, the pivoting the articulating tip is from the longitudinal axis of the wire guide tube 21 and is the same angle alpha ($\alpha$) as an operator reads off of the spaced scale markings 19. In which attitude, as set out above, the drill guide mount barrel 30 will exactly point through the articulating tip cylinder 28.

With the guide 10 configured as shown in FIG. 1, the projecting wire 23 distal end 23a can be projected from the distal end of the articulating arm cylinder 28, as shown in FIGS. 2 and 3. To so extend the projecting wire 23, a proximal end 23b of the projecting wire is connected to a forward end of straight rectangular post section 36 of an actuator slide 35. The actuator slide 35 includes a thumb engaging head end 37, whereby the actuator slide can be moved by a surgeon holding the body 11 and positioning their thumb thereagainst. The actuator slide 35 is moved along a longitudinal track section 38, sliding therealong. Alongside of which track section 38 are scribed markings 39 forming a scale. The projecting wire 23 is thereby projected axially from the articular tip cylinder 28 end to extend, as shown in FIG. 4, across the knee and to engage a point along the distal femur intercondylar notch. For drilling a femoral tunnel section, as set out below, the tibial tunnel containing a barrel 30 fitted through the drill tube mount 20 will thereby align with the located point on the distal femur. In which drilling of the femoral tunnel section, the tibial tunnel can receive the barrel 30, or like drill guide, fitted therein to receive a k-wire turned therethrough end into the distal femur. This k-wire can then receive one or more cannulated drills fitted thereover and turned into the femur, guiding drilling of a straight femoral tunnel section that aligns with the tibial tunnel section.

The extension of the projecting wire 23 is primarily to provide for measuring the distance between the tibial tunnel end within the knee and the location on the distal femur along the intercondylar notch that an end 23a of the projecting wire 23 contacts. Additionally, as appropriate, the projecting wire end 23a can be sharpened for marking as by slightly puncturing that what located point on that will be the femoral ligament point of origin. Such marking can be useful to receive the pointed wire, such as a k-wire, fitted through the drill tube mount 20 barrel 30, or the like, that is turned into and seated in the distal femur for guiding tunnel drilling utilizing at least one cannulated drill.

For the primary purpose of measuring the distance between what will be the tibial and femoral points of ligament origin, a surgeon, holding the guide body 11 in their hand, moves the actuator slide head 37 with their thumb, urging it along track 38, and extending the projecting wire end 23a out from the distal end of the articulating tip 26, as described. By observing the positioning of a slide head forward end 37a, or a marking thereon, not shown, against the spaced scale markings or indicia 39 that are indicative of increments of length or distance, in millimeters, the distance across the knee between what will be the ligament points of origin can be read off of scale 39. This distance determination is utilized along with a determination of the length of the tibial tunnel as determined by the surgeon viewing spaced markings of a scale 30a scribed along the surface of barrel 30 that represent increments of distance, preferably in millimeters, the surgeon can determine the length of tibial tunnel section 49. Knowing the length of the tibial tunnel section, the distance between the ligament points of origin, and knowing the total length of the straight ligament tunnel from the distance a final cannulated drill has been turned into the distal femur endosteum enables a surgeon to choose and appropriate length and configuration of a ligament graft for mounting in the straight ligament tunnel in an anterior cruciate ligament repair procedure. Which replacement ligament can be a natural or prosthetic ligament. To control projecting wire extension out from the articulating tip cylinder 28 end, providing for the projecting wire automatically retracting when the surgeon releases the actuator slide head 37, a coil spring 40 is preferably maintained between the forward face of the actuator slide bottom end section 36, and a stop 41, as shown in broken lines in FIGS. 1 and 3. So arranged, the coil spring 40 is relaxed when the projecting wire 23 is fully retracted, as shown in FIG. 1, and is compressed as the actuator slide 35 is moved to extend the projecting wire end 23a, as shown in FIG. 3. Which extension distance shown as Beta ($\beta$) in FIG. 3, that is the length of travel of the actuator slide 35 travel along the track 38 and is the same distance Beta ($\beta$) that the projecting wire 29 extends outwardly from the end of the articulating tip 26.

In practice, as shown in FIG. 4, the guide 10 body 11 is held by an operator/surgeon, not shown, such that the surgeon's thumb can engage the actuator slide head 37. Initially, with the barrel 30 turned out of the drill tube mount 20, as by turning a barrel broad head end 42, the straight wire guide tube 21, with the articulating tip 26 configured as shown in FIG. 1, is inserted, through an arthroscopic portal incision, not shown, into the patient's knee 45. In this insertion, the articulating tip 26 end travels to a point below the patella 46 and between the distal femur 47 and proximal tibia 48, to approximately align with an end 49a of a tibial tunnel 49, shown in broken lines. The drill tube mount 20 is then moved, by pulling the radial arm 18 out of the end 14 of body 11, into alignment with the tibial tunnel 49 end 49b and the barrel 30 is turned therethrough and into the tibial tunnel 49. Which pulling of the radial arm 18 out of body 11 pulls the connecting wire 22 to pivot the articulating tip 26 to where the cylinder 28 thereof aligns axially with the tibial tunnel. The spike or stylus end 32 of the fin 31 is also pivoted into alignment with so as to fit into and seat in that tibial tunnel end 49a. Thereafter, the surgeon/operator slides the actuator slide 35 head 37 along slot 38, extending the projecting wire 23 across the intra articular joint between the distal femur and proximal tibia. The projecting wire end 23a is to contact and may be use to mark the distal femur surface in the femur intercondylar notch that will be the femoral point of origin of a replacement anterior cruciate ligament. In that projecting wire 23 extension, the surgeon compares an alignment of the actuator slide forward face, or some other indicator such as a straight line marked thereon, to the scale markings or lines 39 scribed on the body 11, alongside track 38, the aligned markings 39 representing the combination of the length of the articulating tip and the length the projecting wire has extended out of the articulating tip that is the spacing distance between the tibial and femoral points of ligament origin. With this spacing distance, and from a determination off from scale 30a formed along the barrel 30 of the drill tube mount 20 and the distance a last cannulated drill was turned into the distal femur, the lengths of the tibial and femoral tunnel sections and the distance between the ligament points of origin across the intra articular joint can be determined. With that determination, the surgeon can then select an appropriate length of natural or prosthetic ligament for use in an anterior cruciate ligament replacement procedure. Thereafter, the actuator slide 35 is returned to its original position, retracting the projecting wire 23 and, with the barrel 30 turned out of the drill tube mount 20, the mount connected to the end of the radial arm 18 can be moved to towards the body 11, extending the connecting wire 22 to return the articulating tip 26 to the attitude shown in FIG. 1, where the cylinder 28 is axially aligned with the wire guide tube 21. The wire guide tube 21 can then be pulled out of the patient's knee. Thereafter the barrel 30, or a like drilling guide tube arrangement can be fitted into the tibial tunnel 49 to guide turning of a wire, such as a k-wire, therethrough and into the distal femur. Which k-wire will pass through the point on the distal femur along the intercondylar notch contacted by the projecting wire end 23a, that will be femoral point of origin of the replacement anterior cruciate ligament, and into the femur. The k-wire can then receive one or more successively larger cannulated drills, not shown, fitted thereover and turned into the distal femur endosteum, forming the femoral tunnel section that is aligned with the tibial tunnel section as a straight ligament tunnel for receiving and mounting a natural or prosthetic ligament therein as a replacement for a patient's damaged anterior cruciate ligament.

While a preferred embodiment of my invention in a tunnel projection drill guide and method for its use for determining a spacing distance between femoral and tibial tunnel ends within a patient's knee for selecting a proper length of replacement natural of prosthetic ligament in an anterior cruciate ligament repair procedure and for, as appropriate, marking a location on the distal femur to receive and k-wire, or the like, turned therein, has been shown and described herein, it should, however, be understood that this disclosure is made by way of example only and that variations to the invention as described are possible within the scope of this disclosure without departing from the subject matter coming within the scope of the following claims and a reasonable equivalency thereof, which claims I regard as my invention.

I claim:

1. An ACL bone tunnel projection drill guide comprising, a body configured to be conveniently held by a surgeon wherein is formed a uniform arcuate shaped cavity extending therein from an end surface for receiving a curved radial arm for travel back and forth therein and including an outer slot formed along a body rear side surface; a curved radial arm; a straight wire guide tube means that is connected at its proximal end at approximately a right angle to an end of a body forward side which said wire guide tube means includes an articulating tip at its distal end and is open therethrough to contain a connecting wire and a projecting wire; a connecting wire with means for connecting a distal end thereof to said articulating tip; means for connecting a proximal end of said connecting wire to said radial arm, whereby when said radial arm is moved along said arcuate shaped cavity, said articulating tip is pivoted from an axial attitude to said wire guide tube, to an angle that is the angle formed between a distal end of said radial arm and said body end wherethrough said radial arm is fitted; a drill tube mount secured across said radial arm distal end that receives a drilling guide barrel fitted therethrough, which said drilling guide barrel aligns with a passage formed through said articulating tip; a projecting wire contained in said wire guide tube means; an actuator slide means fitted to travel within said body rear side surface slot that connects to a proximal end of said projecting wire such that movement of said actuator slide extends and retracts a distal end of said projecting wire out of and back into said articulating tip; and means for determining the distance said projecting wire extends from the distal end of said articulating tip.

2. An ACL bone tunnel projection drill guide as recited in claim 1, wherein the body forward and rear sides are equally spaced with flat top and bottom ends, with the uniform arcuate cavity formed from said bottom end, and the body rear side surface slot is formed along the center of said rear arcuate side and maintains a post section of an actuator to slide therein that includes a slide head secured across a top end thereof and connects to the projecting wire proximal end at a bottom end of said post section.

3. An ACL bone tunnel projection drill guide as recited in claim 2, wherein the means for determining the distance the projecting wire extends from the distal end of the articulating tip is a scale consists of markings representing increments of distance scribed at interval alongside the body rear side slot; and an indicator is provided with the slide head for alignment with one of said scale markings for reading a distance therefrom that is the combined length of said articulating tip and the distance said projecting wire has extended therefrom.

4. An ACL bone tunnel projection drill guide as recited in claim 2, further including spring means arranged in the body between the actuator slide post section bottom end and an opposing body wall, and is for biasing the actuator slide to a bottom of the slot scale where the projecting wire is retracted within the articulating tip.

5. An ACL bone tunnel projection drill guide as recited in claim 1, wherein the means for connecting a distal end of the connecting wire to the articulating tip is a bead secured across said connecting wire distal end; and a pair of spaced walls are secured to said articulating tip at right angles to said connecting wire, with a rear of said walls having a slot formed therein wherealong said connecting wire can be slid, to fit said bead between said walls.

6. An ACL bone tunnel projection drill guide as recited in claim 5, wherein the opposing surface of the pair of spaced walls are each concave forming a cup to receive the bead therein.

7. An ACL tunnel projection drill guide as recited in claim 1, further including, a fin formed as a narrow regular triangle section and is secured along a forward triangle side to the articulating tip surface where an apex of said narrow regular triangle section approximately aligns with the junction of the distal end of the straight wire guide tube means and the proximal end of said articulating tip, and with a junction of a rear side of said narrow regular triangle section and a base of said narrow regular triangle section forming a point; and further including a narrow wall section formed to have a triangular shape with a base thereof secured to said straight wire guide tube means such that a sloping forward wall is juxtapositionied to said fin rear side when said articulating tip is pivoted to where an opening therethrough aligns with the opening through said straight wire guide tube means, and a forward side of said narrow wall slopes into contact with the surface of said straight wire guide tube means.

8. An ACL bone tunnel projection drill guide as recited in claim 1, wherein the connecting wire is fitted between a pair of rollers that are maintained within the body, and said connecting wire proximal end is connected to said radial arm.

9. An ACL bone tunnel projection drill guide as recited in claim 8, wherein the location where the connecting wire proximal end is joined to the radial arm and the mounting of the pair of rollers within the body is such that the articulating tip is axial to the straight wire guide tube means when said radial arm is fully retracted into said body, the connecting wire to extend through said straight wire guide tube means and pivot said articulating tip away from the end of said body as said radial arm is moved out of said body, which said connecting wire extension and resulting articulating tip pivoting is directly proportional to the distance said radial arm is moved away from the end of said body to a limit of radial arm travel.

10. An ACL bone tunnel projection drill guide as recited in claim 9, further including a number of spaced markings scribed at equal intervals along the radial arm as a scale for comparison with an indicator that is formed on the body end wherefrom said radial arm projects, which said scale markings are in degrees to indicate both the degrees of arc the drill tube mount that is secured to the end of said radial arm has moved away from said body end and the angle the articulating tip has pivoted from the axis of the straight wire guide tube.

11. An ACL bone tunnel projection drill guide as recited in claim 1, wherein the barrel for fitting through the drill tube mount is removable and includes spaced distance markings scribe at intervals therealong from zero, at said barrel distal end, and is for use in measuring the length of a tibial tunnel section wherein said barrel is fitted.

12. An ACL bone tunnel projection drill guide as recited in claim 1, wherein the projecting wire is flexible to conveniently bend with pivoting of the articulating tip, and is pointed at its distal end.

* * * * *